United States Patent [19]

Tell et al.

[11] Patent Number: 5,173,749
[45] Date of Patent: Dec. 22, 1992

[54] METHOD AND APPARATUS FOR SPECTROSCOPIC MEASUREMENT OF THE CONCENTRATION OF A GAS

[75] Inventors: Robert Tell; Torbjörn Andersson, both of Göteborg; Stefan Lundqvist, Askim; Henrik Ahlberg, Göteborg, all of Sweden

[73] Assignee: Altoptronic AB, Gothenburg, Sweden

[21] Appl. No.: 634,126

[22] PCT Filed: Jul. 7, 1989

[86] PCT No.: PCT/SE89/00404

§ 371 Date: Mar. 5, 1991

§ 102(e) Date: Mar. 5, 1991

[87] PCT Pub. No.: WO90/00732

PCT Pub. Date: Jan. 25, 1990

[30] Foreign Application Priority Data

Jul. 7, 1988 [SE] Sweden .................................. 8802536

[51] Int. Cl.$^5$ ......................... G01N 21/00; G01J 1/42
[52] U.S. Cl. ..................................... 356/437; 356/433; 356/435; 250/343
[58] Field of Search ............................ 356/432–444, 356/409, 411, 413; 250/343, 344, 350, 351

[56] References Cited

U.S. PATENT DOCUMENTS

| | | | |
|---|---|---|---|
| 3,524,066 | 8/1970 | Blakkan | 356/409 |
| 4,934,816 | 6/1990 | Silver et al. | 356/437 |
| 4,937,461 | 6/1990 | Traina | 356/437 |

FOREIGN PATENT DOCUMENTS

| | | |
|---|---|---|
| 0015170 | 9/1980 | European Pat. Off. . |
| 3633931A1 | 4/1988 | Fed. Rep. of Germany . |
| 2165640A | 4/1986 | United Kingdom . |

OTHER PUBLICATIONS

"Tunable Diode Laser Spectroscopy: An Invited Review," by Eng et al., *Optical Engineering*, vol. 19, No. 6, Nov./Dec. 1980.

"Measurements of Pressure–Broadening Coefficients of NO and O$_3$ Using a Computerized Tunable Diode Laser Spectrometer," by Lundqvist et al., *Applied Optics*, vol. 21, No. 17, Sep. 1982.

"IR–Laser Spectroscopy for Measurement Applications in the Industrial Environment," by H. Ahlberg and S. Lundqvist, Institute of Electrical Measurements, Research Laboratory of Electro-Optics and Lasers, Chalmers University of Technology, Goteborg, Sweden, Dec. 1985.

"Measurements of Electric Field Strength in Gas Insulated High–Voltage Components Using Infrared Diode Laser Absorption Spectroscopy," by Svante Höjer et al., *Applied Optics*, vol. 25, No. 17, Sep. 1986.

"Trace Gas Detection Using 1.3-$\mu$m InGaAsP Diode Laser Transmitter Modules," by Daniel T. Cassidy, *Applied Optics*, vol. 27, No. 3, Feb. 1988.

Primary Examiner—Richard A. Rosenberger
Assistant Examiner—Hoa Q. Pham
Attorney, Agent, or Firm—Merchant & Gould, Smith, Edell, Welter & Schmidt

[57] ABSTRACT

Method and apparatus for spectroscopic measurement of the concentration of a gas in a sample where you detect the intensity of light from a light source (1) passed through the sample (4) and through a reference cell (5) and generates a signal which represents the concentration of the gas. A laser diode (1) constitutes the light source which is locked to the absorption line of the gas at known concentration and pressure contained in a reference cell (5). The laser light with the properly selected wavelength is distributed via optical fibres (2, 3, 6) and/or glass prisms (19, 20) to the reference cell (5) and the sample (4). Non-gas-related transmission variations in the measurement path or in the optics is automatically compensated for by a special laser modulation which generates a time multiplexed reference. The measurement can be performed in a measurement cell incorporating several reflective mirrors (30) to reflect the laser beam several times inside the measurement cell thereby increasing the effective length of the measurement path. The measurement can also be performed using an optical fiber designed so that the surrounding gas or fluid via the evanescent field affects the laser light so that the concentration of the substance in question in the surrrounding fluid or gas can be determined.

14 Claims, 16 Drawing Sheets

METHOD AND APPARATUS FOR SPECTROSCOPIC MEASUREMENT OF THE CONCENTRATION OF A GAS

This invention concerns a method and an apparatus to spectroscopically measure the concentration of a gas in a sample whereby a light of a laser diode is intensity and frequency modulated by a modulation signal to lock the light to an absorption line of a gas within a reference cell of predetermined pressure and concentration. The modulated light is distributed through the gas cell and the reference cell and the intensity of the light passed therethrough is detected. A measurement signal and a reference signal is generated, respectively, representative thereof. The measurement signal is automatically compensated for nongasrelated transmission variations in the measurement path. The harmonics of the measurement signal and reference signal are detected after the nongasrelated transmission variations are compensated for and a concentration signal indicative of the concentration in the gas sample is generated.

BACKGROUND OF THE INVENTION

Tunable diode lasers have quickly become important for high resolution instruments for analysis of molecule spectra. Most of the applications for diode laser spectroscopy have so far been in basic research. Lead salt diode lasers emitting in the wavelength range of 3–30 $\mu m$ have been used to study absorption line parameters and for measurement of molecule constants. The possibility of indirectly determine different parameters such as pressure, temperature, or electrical field strength has also been successfully demonstrated. There has been a relatively small interest for the overtone bands around 1 $\mu m$ since these do not significantly contribute to any new information on the analyzed molecules. The main limitation for practical use of lead salt diode lasers in measurement systems has been the need for cooling of to temperatures below that of liquid nitrogen. AlGaAs and InGaAsP diode lasers emit in the 0.68–1.7 um wavelength range and can operate at temperatures up to 50 degrees centigrade A characteristic of these lasers compared to lead salt lasers is their high intensity modulation index which requires special signal analysis to obtain optimum sensitivity. A large number of molecules of interest in process control and environmental measurement applications have absorption bands in the 0.7–1.7 um range, although, these are relatively weak overtone bands. The superior performance of AlGaAs and InGaAsP lasers compared with lead salt lasers however, more than outweighs this difference and they have great potential to be used in instrumental applications.

A very interesting application is for measurement of oxygen concentration, which has many practical applications, e.g. in the medical area. Today, oxygen is usually measured using different electrochemical methods. For example, semiconductor sensors or the transformation of $O_2$ to secondary products for later detection is frequently used. These methods have several limitations. They don't perform real-time measurements and are usually not suitable in explosive environments and moreover, they often influence the measurand since a small amount of the measured (oxygen) gas is consumed by the measurement instrument. These measurement instruments are also often sensitive to other types of gases or organic pollutions which results in a considerably limited lifetime.

From EP-A1-0 015 170 it is known that by using spectrometers with reference and measurements cells and by using optical fibers or glass prism and gas-tight boxes interference with the surrounding environment is avoided This is true concerning the elimination of unwanted contributions to the measurement result from other paths than the measurement path. However, the problem of eliminating the influence of nongasrelated transmission variations in the measurement path or optical probe is not addressed at all.

In DE-A1-3.633.93 the laser is not locked onto the frequency of the absorption line. Instead, the laser current is modulated and the absorption spectrum is studied. The absorption line is then sampled as the current is modulated to determine the gas absorption. Furthermore, the spectrum is sampled on both sides of the line to measure the nongasrelated attenuation. The signal conditioning is performed directly from the sampled spectrum which results in poor accuracy since the measurement value is the result of the subtraction of two, nearly equal, numbers. This method is the most commonly used to avoid measurement errors from attenuation caused by fog, rain etc.

References

1. R.S. Eng, J.F. Butler, and K.J. Linden, "Tunable Diode Laser Spectroscopy: An Invited Review," *Optical Engineering*, Vol. 19, 1980.
2. S. Lundqvist, J. Margolis, and J. Reid, "Measurements of Pressure-Broadening Coefficients of NO and $O_3$ Using a Computerized Tunable Diode Laser Spectrometer," *Applied Optics*, Vol. 21, 1982.
3. H. Ahlberg and S. Lundqvist, "IR-Laser Spectroscopy for Measurement Applications in the Industrial Environment," Institute of Electrical Measurements, Research Laboratory of Electro-Optics and Lasers, Chalmers University of Technology, Goteborg, Sweden, 1985. (7th International Conference on Laser Spectroscopy, SEICOLS 85, Maui, Hawaii, USA, 1985; In Laser Spectroscopy VII, Springer Series in Optical Sciences; Springer Verlag Berlin, 1985.)
4. S. Höjer, H. Ahlberg, and S. Lundqvist, "Measurements of Electric Field Strength in Gas Insulated High-Voltage Components Using Infrared Diode Laser Absorption Spectrosocpy," *Applied Optics*, Vol. 25, 1986.
5. D.T. Cassidy, "Trace Gas Detection Using 1.3-$\mu M$ InGaAsP Diode Laser Transmitter Modules," *Applied Optics*, Vol. 27, 1988.
6. G. Boisde, G. Chevalier, and J.-J. Perez, Demande de Brevet European 0 015 170 Al, European Patent Office, Jan. 18, 1980.
7. K. Cerff, H. Giraud, and G. Krieg, Offenlengungsschrift DE 3633931 Al, Deutsches Patentamt, Bundesrepublik Deutschland, Oct. 4, 1986.
8. G.D. Pitt, D.N. Batchelder, and R.E. Jones, UK Patent Application GB 2 165 640 A, Oct. 13, 1984.

Purpose and significant characteristics of the Invention

The present invention provides a spectroscopic method for measuring the concentration of a gas in a gas sample. A light of a laser diode is frequency and intensity modulated by a modulation signal to lock the modulated light to an absorption line of a gas within a reference cell of a predetermined pressure and concentration. The modulated light is passed through the gas sample along a measurement path and through the reference cell. The intensity of the light passed through the gas sample and the reference cell is detected and a measurement signal and a reference signal, respectively, are generated representative thereof. The measurement signal is automatically compensated for nongasrelated transmission variations in the measurement path by a first and second modulating step. In the first demodulating step, a first difference signal between a monitoring signal representative of the modulated light and the measurement signal is formed. A second different signal between the monitoring signal and the reference signal is also formed. A first and second gain level of the measurement signal and the reference signal, respectively, is automatically adjusted such that the first and second difference signals are equal to zero with respect to an amplitude of a fundamental frequency of the modulation signal. In the second demodulating step, the harmonics of the measurement signal and reference signal are detected with respect to the fundamental frequency of the modulation signal. The compensated and demodulated measurement and reference signal are received and a concentration signal is generated which is indicative of the concentration of the gas in the gas sample.

In another embodiment, the laser light of a laser diode is frequency and intensity modulated by performing stepwise modulation with a modulation signal. After the measurement signal and reference signal are automatically compensated, the measurement signal and reference signal are sampled at corresponding points on an absorption spectrum. The sampling is received and a concentration signal which is indicative of the concentration of the gas in the gas sample is generated.

In addition, an apparatus for spectroscopic measurement of a concentration of a gas in a gas sample is described. The apparatus includes means for intensity and frequency modulating a light of a laser diode by a modulation signal to lock the light to an absorption line of a gas within a reference cell of a predetermined pressure and concentration. The modulated light is provided through the gas sample along a measurement path and through the reference cell by a means for distributing modulated light. A detector detects the intensity of the light passed through the gas sample and the measurement cell and a measurement signal and reference signal, respectively, are generated. Means are provided for automatically compensating the measurement signal for nongasrelated transmission variations in the measurement path. The compensation means includes circuitry for forming a first difference signal between the monitoring signal from a monitor diode representative of the modulated light from the laser and the measurement signal. Means are also provided for forming a second difference signal between the monitoring signal and the reference signal. Circuitry automatically adjusts a first gain level of the measurement signal and second gain level of the reference signal such that the first and second difference signals are equal to zero with respect to an amplitude of a fundamental frequency of the modulation signal. A detector detects the harmonics of the measurement signal and the reference signal with respect to the fundamental frequency of the modulation signal and a compensation signal indicative of the concentration of the gas in the gas sample is generated after receiving the compensated signal and reference signal.

DESCRIPTION OF THE DRAWINGS

The invention will in the following be described with reference to the enclosed drawings.

DESCRIPTION OF THE INVENTION

Figure 1:
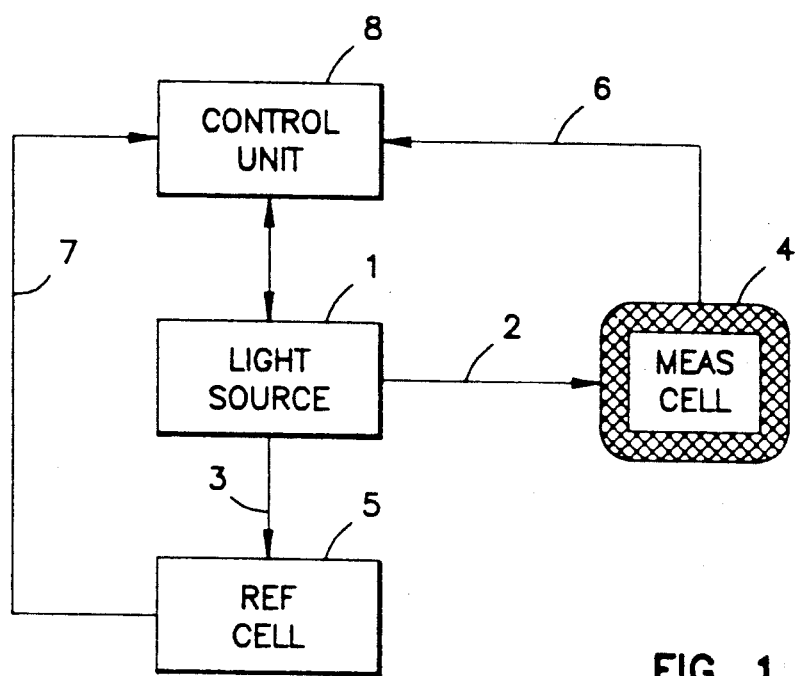
FIG. 1 shows a schematic of the electrooptical gas sensor according to the invention.

The invention concerns a method to analyze gases, e.g. oxygen, using a laser diode spectrometer. A special signal conditioning method for diode laser spectrometers, based on diode lasers with high intensity modulation index, has been developed. Interference from non-gasrelated transmission variations such as fog, rain turbulence and varying transmission through the optics of the apparatus caused by dust particles, condensation etc. is taken care of by the intensity modulation compensation in a unique manner. Interference from gases not contained in the measurement volume is eliminated by using glass waveguides in the instrument. The measurements can be performed over an atmospheric path, in an integrated measurement volume to which the gas is transferred using e.g. tubes, using the evanescent field of an optical fiber surrounded by a medium containing the gas to be measured, or in a special measurement cell, a uniquely designed optical probe to which the light is passed in optical fibers.

A measurement cell, a self-aligned optical probe that is sufficiently small to be integrated in e.g. the mouth piece of a patient and still gives a measurement path of sufficient length to perform accurate measurements of oxygen, has been developed specifically to be used with the spectrometer.

The instrument is designed so that all measurements of different parameters is automatically calibrated if you know the corresponding parameters for the gas in question in a reference cell. This also includes the elimination of influences from fog, rain, dust or condensation in the measurement volume or in the optics of the instrument itself. This means that you are independent of published numbers on line strength etc. A special compact reference cell that can be included on e.g. a simple standard europe-circuit board has been developed. The measurement results from the measurement volume (atmospheric path, optical probe or evanescent fiber probe) are compared with the corresponding results from the reference cell. The gas concentration is computed from two lengths (those of the reference cell and the measurement path) and the known concentration in the reference cell. This results in a very simple calibration procedure and high measurement accuracy.

Below is a list of a number of application areas for the invented diode laser spectrometer.

Medical applications a) Measurement of the oxygen concentration in breathing air. Here a special optical measurement probe has been developed that can be incorporated in e.g. a respirator. The optical probe is connected to the mouth piece at the patient and the light is passed to the probe using optical waveguides (optical fibers).

b) Control of anesthetic gases during operation.

c) Control of oxygen or humidity in an incubator.

d) Studies of metabolism. Here an isotope gas can be used since the high resolution of the instrument is sufficient to discriminate this from the natural abundance of the gas.

e) Pharmaceutical production. Inert packaging of medicals.

Industrial applications f) Safe measurements of oxygen or other gases in explosive environments such as petrol supplies, oil tankers etc. The light is passed to and from the optical measurement probe using optical waveguides. The probe can also be located in environments with strong electromagnetic interference effects such as in a radar set.

g) Measurement of gas concentration in environments with strong radar or radio interference. This means that the laser diode spectrometer can be incorporated in a levelmeter based on microwave technology.

h) Control the presence of oxygen in inert environments.

i) Control of combustion processes.

j) Automotive industry; analysis of exhaust gases, control of air/fuel mixtures.

k) Heating and electricity producing plants; control of combustion, minimization of pollution.

l) Gas production.

m) Lamp manufacturing.

n) Semiconductor industry; control of gas concentration in different processes, in ovens, gloveboxes etc.

o) Process control in annealing and oxidation ovens.

p) Control of fermentation processes.

q) Food industry: beer production, packaging.

r) Measurement of temperature profiles in oxygen containing atmosphere in process ovens.

s) Measurement of pressure in gases t) Measurement of pressure in processes, tanks etc.

u) Galvanic insulated measurements of electrical field strength.

v) Measurement of gas concentrations in fluids, e.g. gases in a battery or the oxygen contents in a lake or sea using an evanescent fiber probe.

x) Measurement of leakage from gas tubes by using an evanescent fiber probe that is deployed in parallel with the gas tube.

Diode laser spectroscopy has traditionally been used to analyze the fundamental IR-band at 3-30 $\mu$m. Laser light is selectively absorbed at frequencies $v_1$ $v_2$ $v_3$ ... which corresponds to fundamental rotational and vibrational transitions. The lasers that have been used in this wavelength range are complicated and expensive. A large number of molecules have combination and overtone bands of the $2v_1+v_2$ type in the wavelength range 0.7-1.7 $\mu$m. These bands usually don't contribute any new information about molecular constants but are well suited for measurements of the concentration of the absorbing gas. This is especially true since in this wavelength range there exists a large number of inexpensive high quality lasers.

In the following, measurement of oxygen is used to illustrate the principle of operation of the invention.

The oxygen molecule has a number of weak absorption bands generated by magnetic dipole transitions. These bands are located around 630, 690, and 760 nm. The A-band of oxygen covers the wavelength range of 759-771 nm and is relatively free from interfering molecules and is suitable for measurement of oxygen using electrooptic techniques. AlGaAs or InGaAsP lasers are suitable light sources for measurements based on selective absorption of light by discrete molecule lines since they have good spatial and temporal coherence. By using oxygen at known concentration and pressure in a reference cell a normalization signal is obtained and also the laser can be locked to the absorption line of oxygen. This enables very accurate measurements of the oxygen concentration in the measurement volume.

AlGaAs, InGaAsP and other semiconductor lasers can easily be frequency modulated by means of the injection current and can therefore be used in differential spectroscopy to obtain a good signal-to-noise ratio. Another characteristic of these lasers, compared with e.g. lead salt lasers, is that apart from the frequency modulation a considerable intensity modulation is obtained at the frequency modulation that is optimum for spectroscopic measurements. The intensity modulation is used to eliminate the influence of nongasrelated absorption in the measurement volume or in the instrument itself without having to use the baseline of the absorption spectrum. This provides superior stability and accuracy. When one measures atmospheric gases it is important to eliminate absorption in air paths to and from the measurement volume. By using glass prisms or optical fibers this unwanted absorption can be avoided.

FIG. 1 shows a schematic of the electrooptical gas sensor according to the invention where 1 is a light source, a laser diode, from which the light is distributed in optical waveguides 2 and 3 to a measurement cell 4, which can be an optical probe or an atmospheric path, and to a reference cell 5. The measurement cell 4 and the reference cell 5 is connected with a control unit 8 using optical waveguides 6 or electrical cables 7.

Figure 3A:
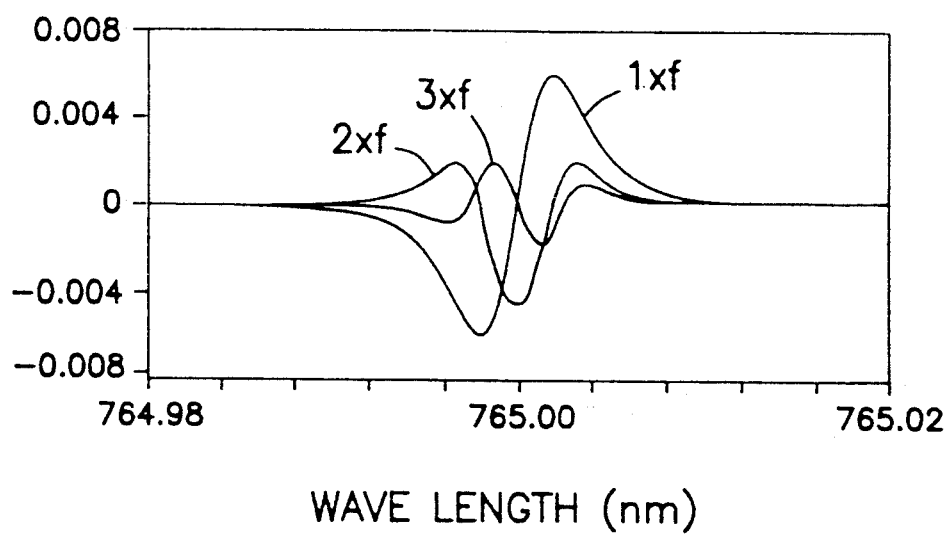
FIG. 3a shows computed signals after compensation for the intensity modulation of the laser and the following lock-in detection.

The reference cell 5, which contains oxygen at known concentration, pressure, and temperature, provides the parameters necessary to lock the wavelength of the light source to the absorption line, and the parameters necessary to calculate the gas concentration, the temperature, pressure, and electric field strength. This is performed according to the following. A triangular AC-current with frequency $f_o$ is added to the laser bias current. The bias current is adjusted so that the average wavelength of the laser coincides with that of the absorption line. The light source 1 will, due to the added AC-current, change its wavelength (frequency modulated) with the frequency $f_o$ around the averaged value set by the bias current. The light, now frequency modulated around the center of the absorption line of the gas, is passed through the measurement cell (an atmospheric path, an optical probe, or an evanescent fiber) and is thereafter detected. By feedback of the signal of $3f_o$ via an analog regulator to the laser bias current the wavelength of the light source 1 is stabilized to the center of the absorption line. The light from the light source 1 is divided into branches, one which is passed to the reference cell 5, and one which is passed using optical waveguides 2 to the measurement cell. The measurement signal is then passed back and lock-in detected at frequency $2f_o$. When the light source is modulated with a frequency $f_o$ and the signal from the detector is demodulated with the frequency $2f_o$, this signal looks according to FIG. 3a. The signal 2×f in FIG. 3a is proportional to the gas concentration.

Apart from the variation in absorption caused by variations in the concentration of the measured gas there will be variations in the transmission caused by changes in the transmission of the optics due to rain, dust, or humidity or when the received signal after the measurement path varies due to turbulence, rain, and fog etc. Normally, this is compensated for by measuring the baseline of the absorption spectrum and make a normalization. This baseline value however, is a slowly varying signal with a very low lower frequency limit which imposes drift problems. Furthermore, preamplifiers designed to accommodate these low frequencies have much less sensitivity than AC-coupled amplifiers operating with a small bandwidth.

In measurements of gas concentrations it is very important to compensate for absorption that can arise in air paths that exist in the distribution of the light to and from the measurement area. By using glass prisms or optical fibers this unwanted absorption can be eliminated. Furthermore, it is also important to compensate for varying transmission in the instrument itself or in the measurement path that is not related to the measured gas. This can be achieved using a signal conditioning which identifies this component and compensate for it without having to use the baseline of the absorption spectrum. This technique provides superior stability and measurement accuracy.

Figure 2:
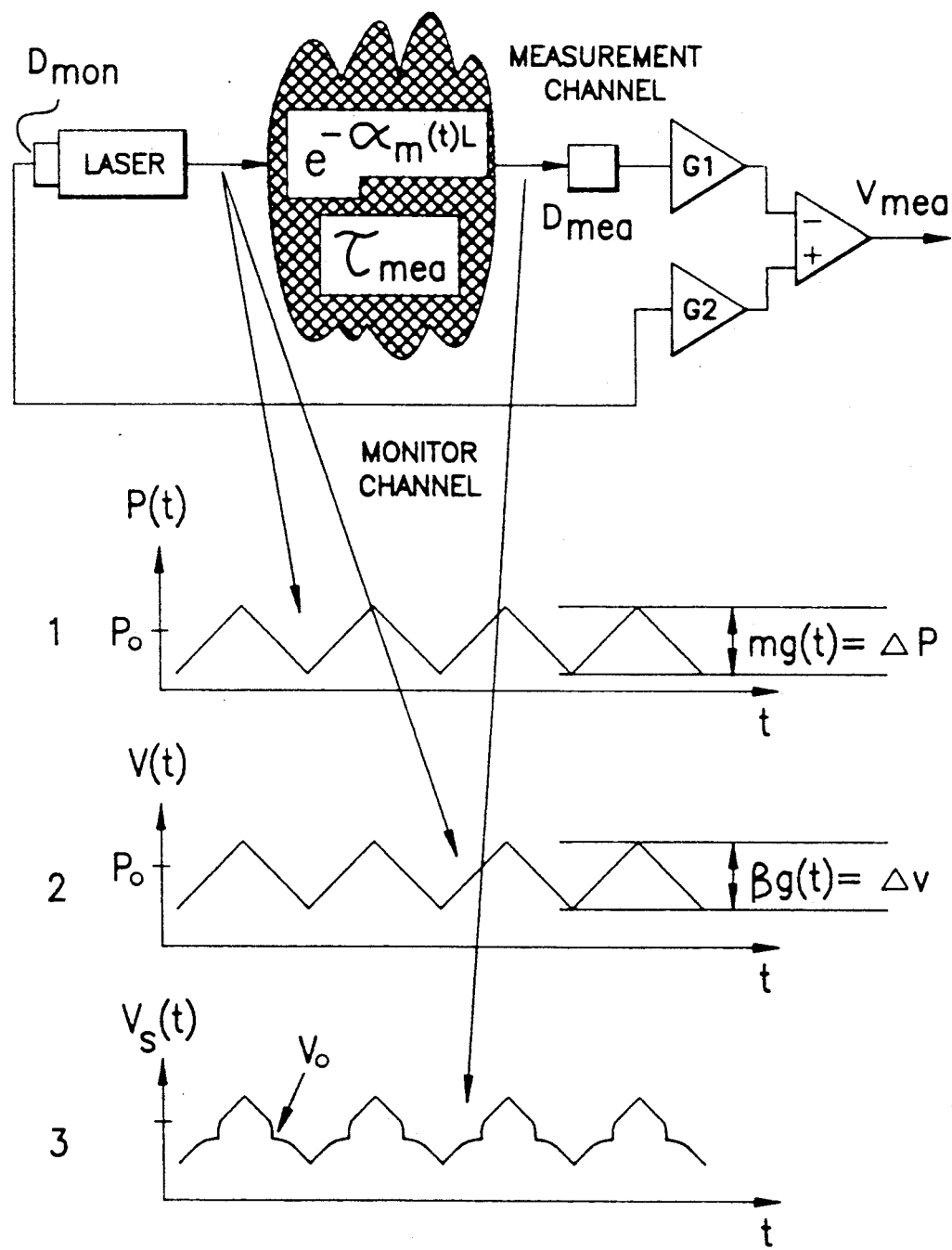
FIG. 2 shows the measurement method with the used modulation signals and the corresponding detected waveforms after absorption in the measured gas. Specifically, the intensity modulation of the laser, the frequency modulation of the laser, and the detected intensity variation after passage of the measurement volume are illustrated.

In the system according to the invention a signal proportional to the atmospheric transmission is generated by sampling at the peak of the received triangularly shaped optical signal. The peak value is compared with the signal from the monitor photodiode. The peaks of the triangular signal is well separated from the absorption peak as illustrated in FIG. 2. The relative size of the absorption peak is usually much smaller than what is shown in the figure. This method of measuring both on the peaks of the triangular signal and on the absorption line generates a measurement reference that automatically experiences the same transmission losses as the light absorbed by the absorption line since by definition the beams are coaligned.

A "dual-beam spectrometer" has been realized by time-multiplexing of one measurement beam. In ref. 7, as listed in the Background of the Invention section, the absorption is determined from sampling directly in the absorption spectrum around the line. However, no modulation technique is used. The drift problems of this type of instrument is considerably large. In our method it is very easy to calculate the gas concentration using a normalization procedure considering that we know the gas concentration in the reference cell. The concentration is computed from the lengths of the path in the measurement and reference cell and from the measured detector signals from the measurement and reference channels as well as the gas concentration in the reference cell.

This method differs considerably from those used in ref. 6, 7, and 8, as listed in the Background of the Invention section, where the laser light, which is unmodulated, is slowly varied around the absorption line and the resulting spectrum is sampled relative to the baseline. Normally, this is the method used to compensate for nongasrelated transmission variations. The signal conditioning method according to the invention, which has been described here, performs all signal conditioning at high audio frequencies, resulting in superior stability, measurement accuracy and sensitivity.

To determine the pressure in the measurement volume we proceed according to the following. Since the width of the absorption line depends on pressure and temperature one parameter has to be isolated if we are going to be able to determine the other. We let the wavelength of the light source sweep over the absorption line. The light is then detected after passage through the gas and the width and the integral of the absorption line is measured simultaneously. The result of the integration gives the integrated line strength which is a parameter whose temperature dependence is known and is available in the literature. Since the pressure and temperature in the reference cell 5 is known, the pressure in the measurement volume can be calculated.

Figure 7:
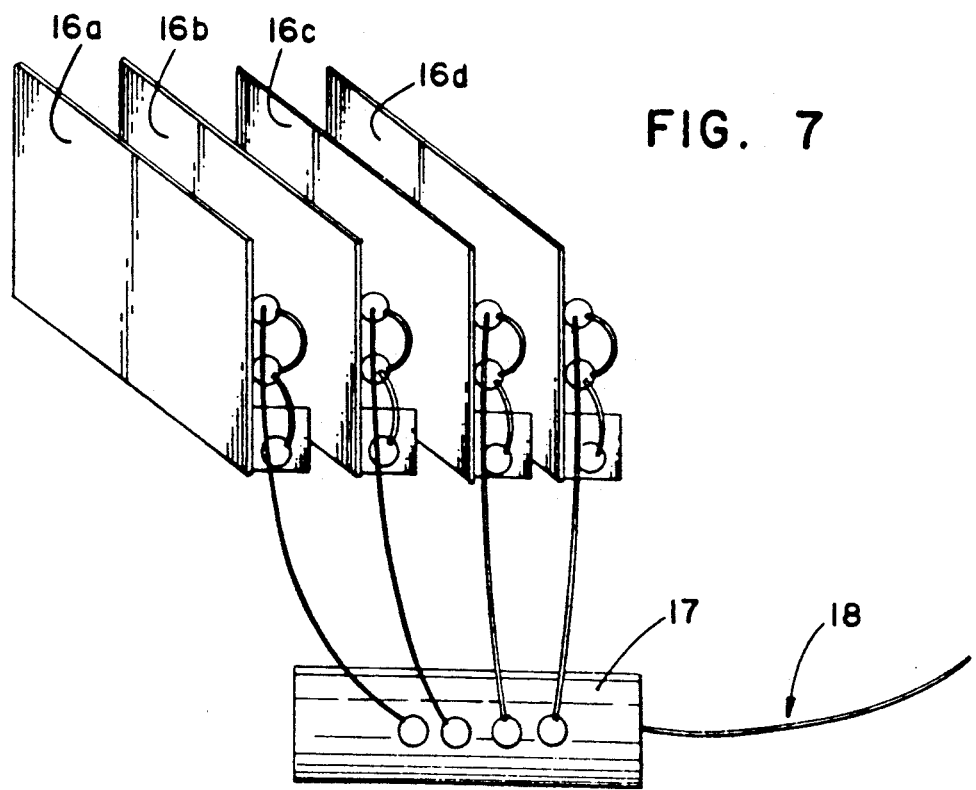
FIG. 7 shows a system with one laser circuit which is multiplexed to several fibers for simultaneous measurements of one gas over several different measurement paths.

The temperature can be measured with high accuracy by using two laser circuits where the lasers are locked to two different rotational transitions in e.g. oxygen. The laser light from the cards are multiplexed together in an optical fiber as shown in FIG. 7 and the combined light is passed to the measurement volume. The temperature is then calculated from the difference in absorption in the two wavelengths. This is a new way to apply Mason's method. In this way the temperature can be measured locally and intrinsically safe using the optical probe or alternatively, the average temperature over an atmospheric path can be determined.

An electrical field strength is measured in a similar way by sweeping the laser wavelength over the absorption line. In the presence of an electrical field in the gas the absorption maximum will be changed or displaced in wavelength. Since we know the position and strength of the absorption line in the reference cell 5, this displacement can be determined which is a measure of the electrical field strength.

Strong magnetic fields results in a direct modulation of the gas concentration in a paramagnetic gas as oxygen. The variation in gas concentration gives a direct measure of the magnetic field variations. With the spectrometer configured for a free measurement path field variations between different paths can be analyzed.

It is usually advantageous to a large extent to use digital electronics to generate the modulation and reference signals in the laser diode spectrometer. For instance it is easier to obtain a high degree of phase stability compared to an analog solution and moreover, it is easier to digitally control the frequency and phase.

It is also advantageous to use a (digital) square-wave signal to demodulate the measurement and reference signals in the spectrometer. This avoids a square-wave to sinus-wave transformation which if performed with analog technique can lead to drift in the phase and decreased measurement accuracy. Traditionally, the modulation signal in laser diode spectrometers has been a sine-wave but it would be a clear advantage if a simpler waveform could be used. An ideal alternative would be a triangular wave which is easy to generate from a square-wave with an AC-coupled integrator.

FIG. 2 illustrates the signal conditioning used in the invention. The laser is modulated with the current $$i(t) =$$

$i_0[1 + g(t)]$ where $g(t)$ is a triangular wave with the amplitude $a_0$

The laser will be modulated both in intensity (FIG. 2:1), $P_L =$ $P_0[1 + mg(t)]$ and in frequency (FIG. 2:2), $v_L = v_0[1 + \beta g(t)]$ with the frequency $f_0$. Here, $m$ = intensity modulation index of the laser and $\beta$ is the frequency modulation index.

When the optical signal sweeps over the absorption line of the measured gas its frequency modulation will transform into an amplitude modulation according to $$a_m(t) = Sc_m N_L/\pi \cdot \sqrt{273/T} \cdot v_B/[(\beta g(t))^2 + \Delta v_B^2]$$

here S, $N_L$ and $\Delta V_B$ are constants of the molecule line and $c_m$ is the gas concentration.

A composed signal with the fundamental frequency $f_o$ is obtained according to FIG. 2:3

$$V_s(t) = G_1 P_o \tau_{mea} (1 + m\ g(t)) (1 - a_m(t)\ L_{mea})$$

The AC-component of this signal is $$V_s(t) = G_1 P_o \tau_{mea} [m\ g(t) - (1 + m\ g(t))\ a_m(t) L_{mea}]$$

The signal in the measurement channel is now substracted with the monitor signal which after AC-coupling can be expressed as $$v_{mon}(t) = G_2\ P_o\ m\ g(t)$$

The detected measurement signal now has the form $$V_{mea}(t) = G_2 P_o\ m\ g(t) - G_1\ P_o\ \tau_{mea}[m\ g(t) - (1 + mg(t))a_m(t)L_{mea}]$$

This signal is sampled at the peaks of the triangular wave and thereafter the analog signal conditioning unit adjusts the gain $G_1$ so that $$V_{mea}(nT) = G_2 P_o\ m\ g(nT) - G_1 P_o \tau_{mea}[mg(nT) - (1 + mg(t))a_m(nT)L_{mea}]$$

which results in $$G_1 = \frac{G_2 mg(nT)}{\tau_{mea}[mg(nT) - \{1 + mg(nT)\}a_m[nT]L_{mea}]}$$

In all practical applications the residual term due to the extension of the absorption line out to the peak of the triangular wave will be neglectable and the expression for $G_1$ becomes $$G_1 = G_2/\tau_{mea}$$

Consequently, with this method the system will automatically compensate for variations in transmission in the measurement path. The measurement signal after this compensation is $$V_{mea} = G_2\ P_o(1 + m\ g(t))a_m[t]L_{mea}$$

Figure 10A:
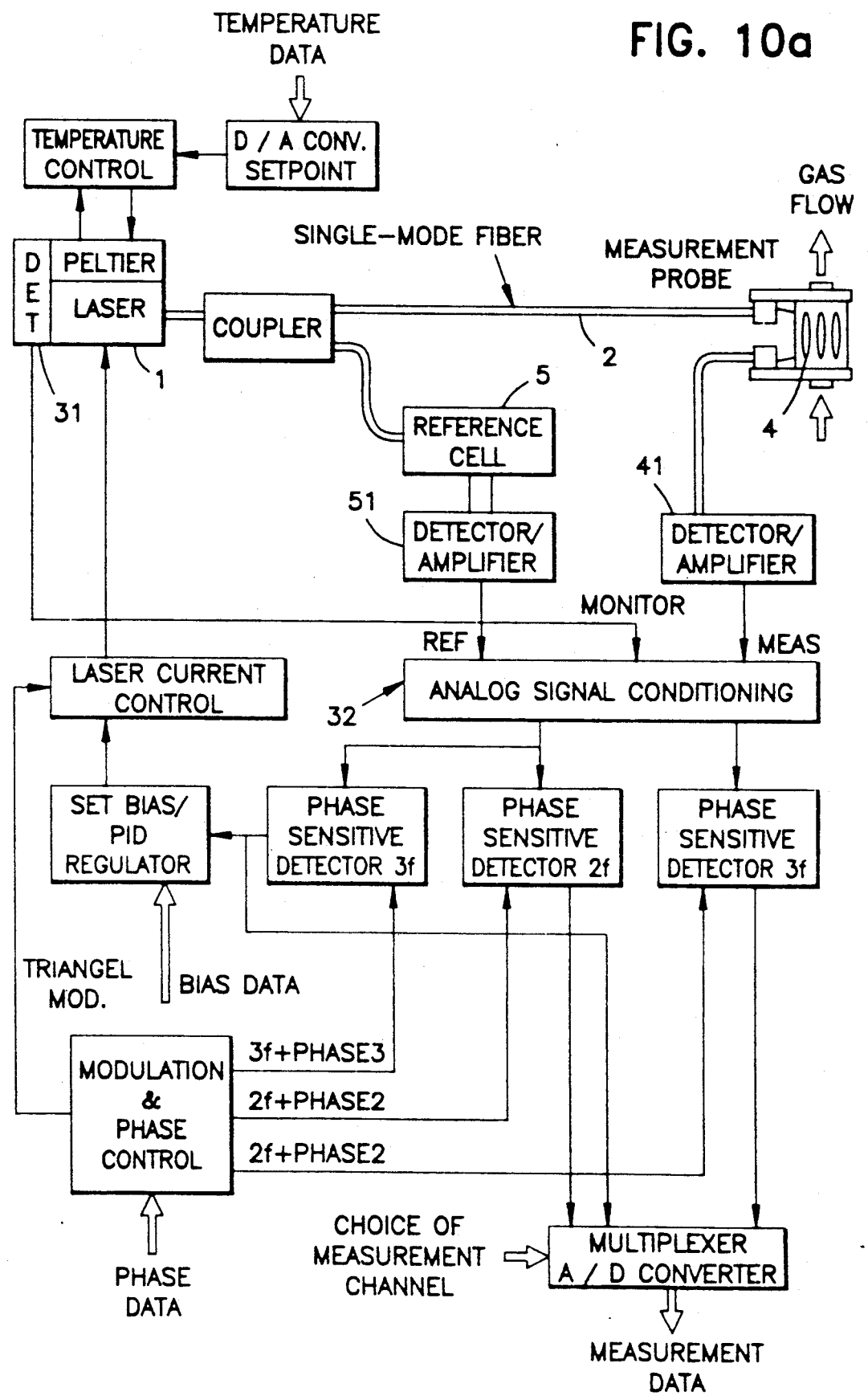
FIG. 10a and FIG. 10b, collectively referred to herein as FIG. 10, show a block diagram of the measurement system including transmission compensation and lock-in detection.
Figure 10B:
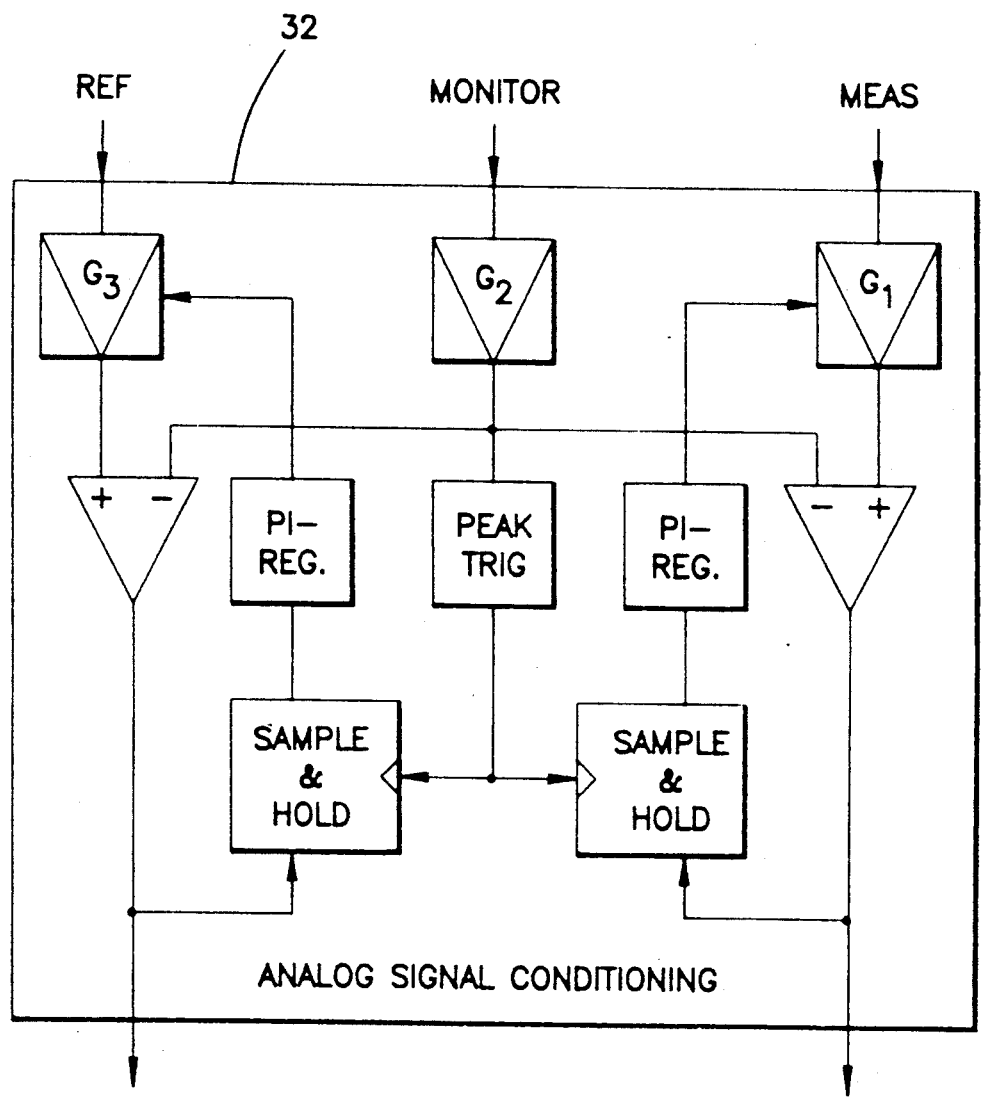

The measurement signal is demodulated in two steps according to FIG. 10. The first step is the analog signal conditioning unit with the transmission compensation described above. In step two the compensated measurement signal is synchronously demodulated using a square-wave. The compensated measurement signal is divided according to its frequency components $$v_{mea}(t) = G_2 P_0 L_{mea} \left\{ 1 + m8/\pi^2 \sum_{j=1,3,5}^{\infty} \{[-1]^{(j-1)/2}\}/j^2 \cos[j(wt + \theta)] \right\} \cdot \sum_{i=0}^{\infty} H_i(\overline{v})_m \cos[iwt]$$

By multiplying with a square-wave of frequency $2f_o$ and perform a low-pass filtering the final signal is obtained $$v_{mea} = G_2 P_0 L_{mea}\{H_2(\overline{v})_m + m8/\pi^2[(H_1(\overline{v})_m + H_3(\overline{v})_m)\frac{1}{2}\cos[\theta] - H_1(\overline{v})_m/18\cos[3\theta] + H_3(\overline{v})_m/50\cos[5\theta]]\}$$

The phase $\theta$ is adjusted to minimize the interference term. In this case $m \approx 6\%$. In the vicinity of the line center $v = v_o\ H_1(\overline{v})_m$, $H_3(\overline{v})_m \approx 0$ and thus the measurement signal after lock-in detection becomes $$v_{mea} = G_2\ P_o\ L_{mea}\ H_2(\overline{v})_m$$

In the same manner, the signal from the reference detector finally becomes $$V_{ref} = G_2 \, P_o \, L_{ref} H_2(\bar{v})_r$$

These two signals are sampled, A/D-converted and divided in the computer $$V_{mea}/V_{ref} = G_2 \, P_o \, L_{mea} \, H_2(\bar{v})_m / \, G_2 \, P_o \, L_{ref} H_2(\bar{v})_r$$

The signal $H_i(\bar{v})_m$ is proportional to the gas concentration $c_i$ and the laser diode spectrometer calculates the gas concentration in the measurement path as $$C_{mea} = [v_{mea}/v_{ref}][L_{ref}c_{ref}/L_{mea}]$$

The constants $L_{ref}$ and $c_{ref}$ are known while $L_{mea}$ either is measured separately or using the spectrometer. This can be achieved by measuring the phase difference between the reference and measurement signal from which a signal proportional to $L_{mea}$ can be obtained. This means that the instrument after calibration by itself can measure all data necessary to calculate the gas concentration.

A computer simulation has been made to verify the function of the laser diode spectrometer. The following parameters have been used.

| Parameter | Typical value | Range | Unit |
|---|---|---|---|
| Modulation frequency, w/2π | 10 | | kHz |
| Laser modulation IM, m | 0 | 1 | % |
| Laser modulation FM, $2\beta_{LF}$ | 5 | 1-20 | GHzp-p |
| Thermal cutoff frequency | 10.1 | | kHz |
| Absorption at $v_O$, $a(v_O)L$ | 2 | 1-3 | % |
| Pressure broad.coeff.(HWHM), $\Delta v_B$ | 1 | | GHz/atm |
| Pressure, p | 1 | 0.5-1.5 | atm |
| Temperature, T | 273 | | Kelvin |
| Absorption wavelength | 765 | | n m |
| Laser center wavelength | 765 | +−0.02 | n m |
| Phase error, reference signal | 0 | 0-90 | degrees |

Figure 3B:
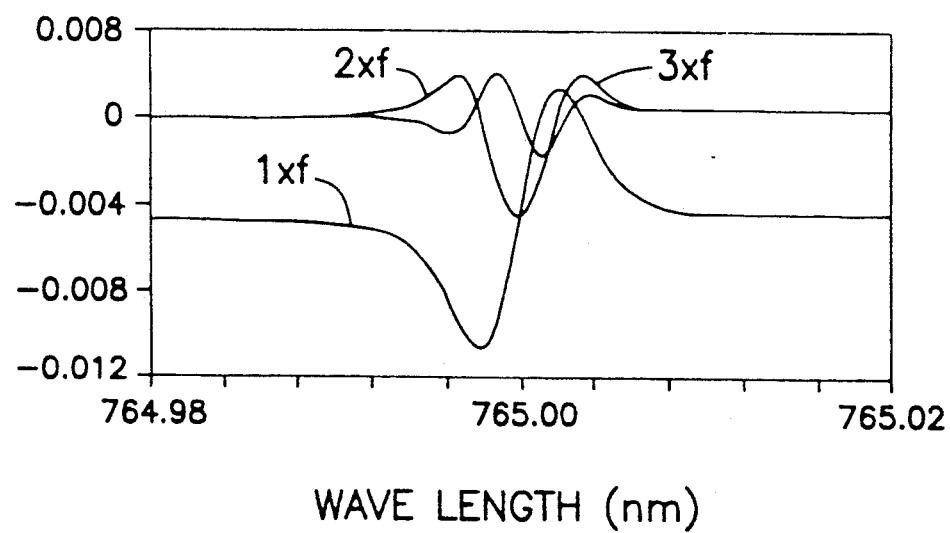
FIG. 3b is the same as FIG. 3a but in this case for an incomplete intensity compensation resulting in a remaining intensity modulation of 1%.

A triangular wave is generated directly from a digital control unit using an integrating OP-amplifier. The laser bias current is adjusted so that the laser light is absorbed in the gas molecules at the zero crossings of the triangular wave. This triangular wave modulates the laser intensity according around $P_o$ accordingly to FIG. 2, curve 1 and the laser frequency around $v_o$ according to curve 2 at a frequency $f_o$. After passage through the gas volume a measurement signal according to curve 3 in FIG. 2 is obtained. The gain $G_1$ is automatically adjusted as previously described and the resulting measurement signal is obtained after substraction of the monitor signal. Lock-in detection at $2f_o$ and $3f_o$ with digital reference signals provides the final measurement signal and feedback signal. This leads to a straight forward instrumental design and provides higher sensitivity compared with the conventional approach using sine-waves. The detected signals from an absorption line at the different lock-in detection frequencies are shown in FIG. 3a. From FIG. 3b it is apparent that only $3f_o$ is suitable for locking of the laser, since this signal is insensitive to remaining intensity modulation after the first demodulation step.

Figure 3C:
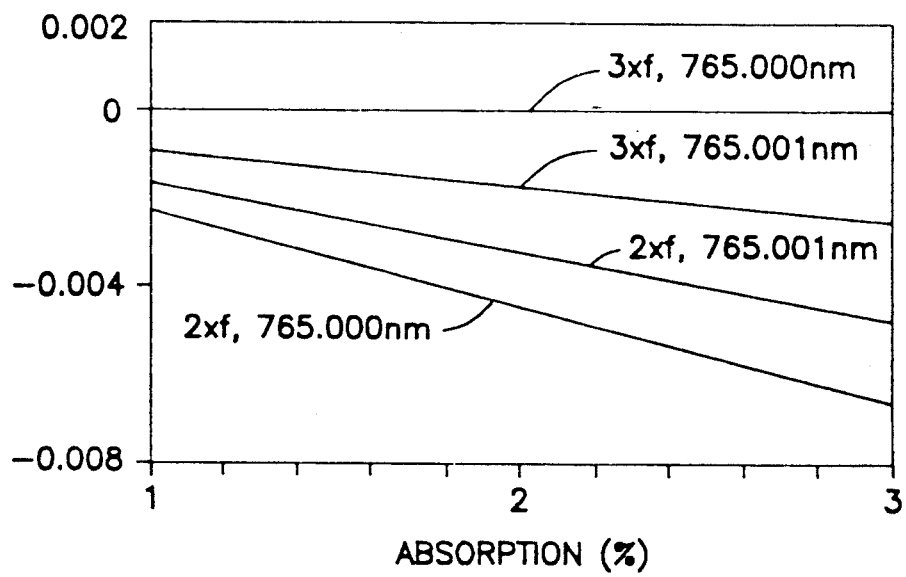
FIG. 3c shows the measurement signal as a function of the gas concentration after signal conditioning.
Figure 3D:
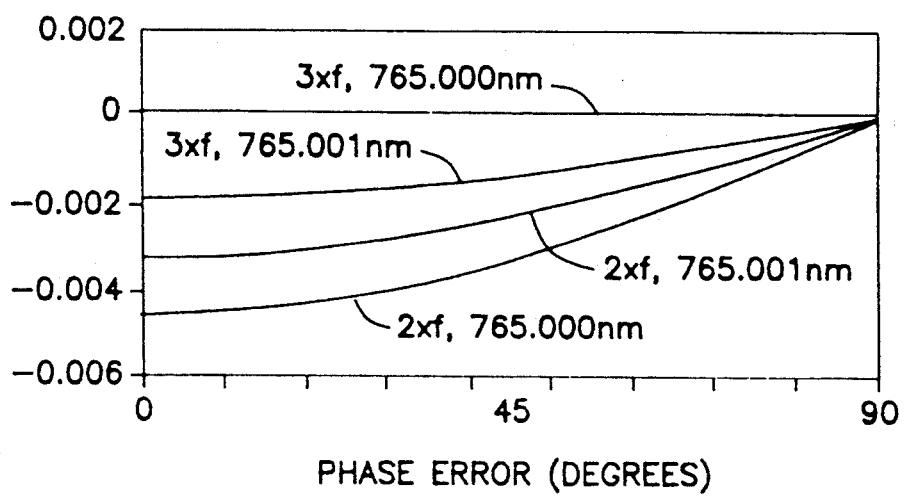
FIG. 3d shows how the output from the laser spectrometer varies with phase error in the lock-in detection.
Figure 3E:
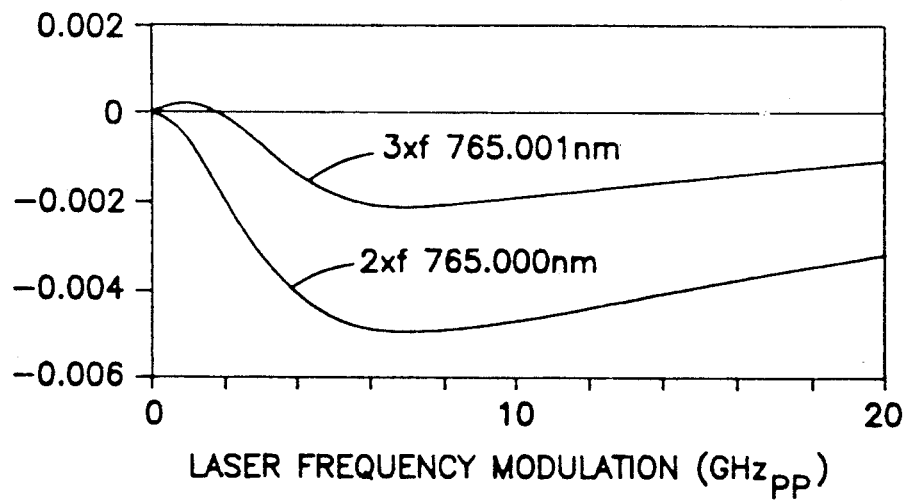
FIG. 3e shows the output signal from the laser diode spectrometer as a function of the laser's frequency modulation.
Figure 3F:
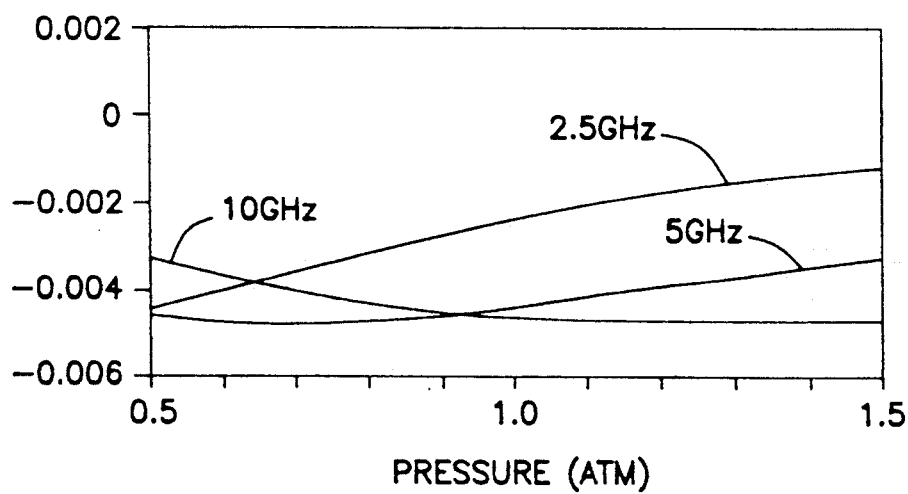
FIG. 3f shows the output from the laser spectrometer as a function of the total pressure in the measurement volume.

FIG. 3c shows that by using this signal conditioning method a linear response for gas concentration measurements is obtained.

The measurement itself is performed in a measurement volume that might be an atmospheric path, an evanescent optical fiber, or an optical probe that in a small volume creates a suitable absorption path. The distribution of light both to and from the probe can be performed with optical waveguides. This means that the sensor part of the instrument is entirely optical and is very suitable in potentially explosive or electrically disturbed environments. Moreover, the attenuation in optical fibers is very low. The sensor can be located several kilometers from the control electronics.

Figure 4:
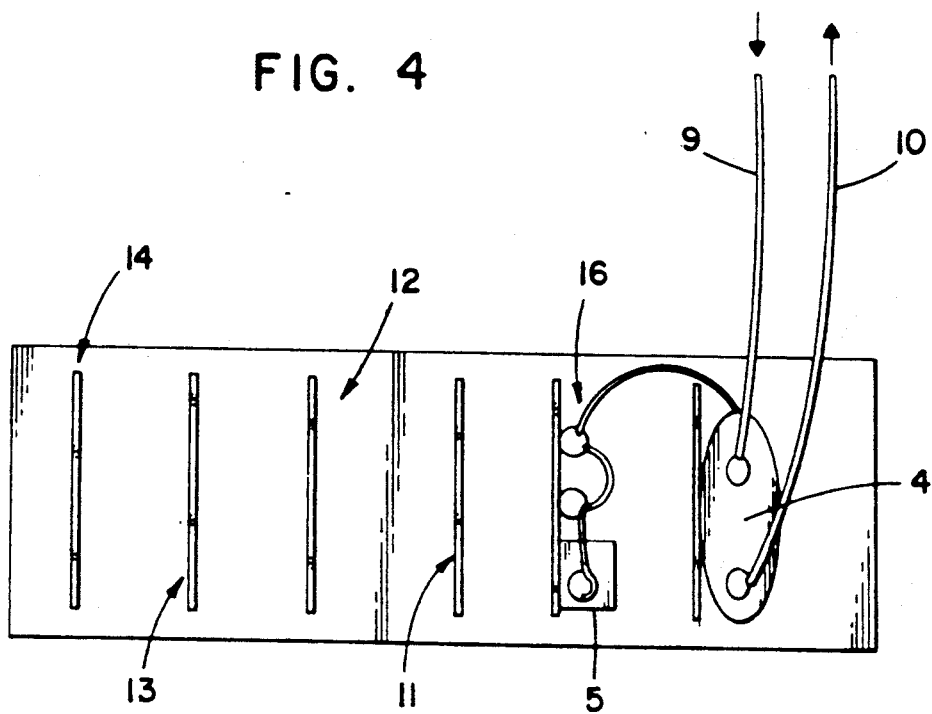
FIG. 4 shows the basic structure of the instrument using optical fibers according to one embodiment of the invention.

Using optical fibers provides a flexible instrument which may be of modular design according to FIG. 4 which shows a measurement cell 4 integrated in the diode 'laser spectrometer. Laser light source 1, measurement cell 4, and reference cell 5 can be placed in an instrument box. The different modules can be constructed on standard europe circuit boards in a standard 19" rack. The measurement cell is located inside the instrument and the gas to be analyzed is led to it using flexible hoses 9 and 10. Other parts of the system includes a modulation and control unit 11, a laser and peltier driver 12, an interface 13 and power supply 14.

Figure 5:
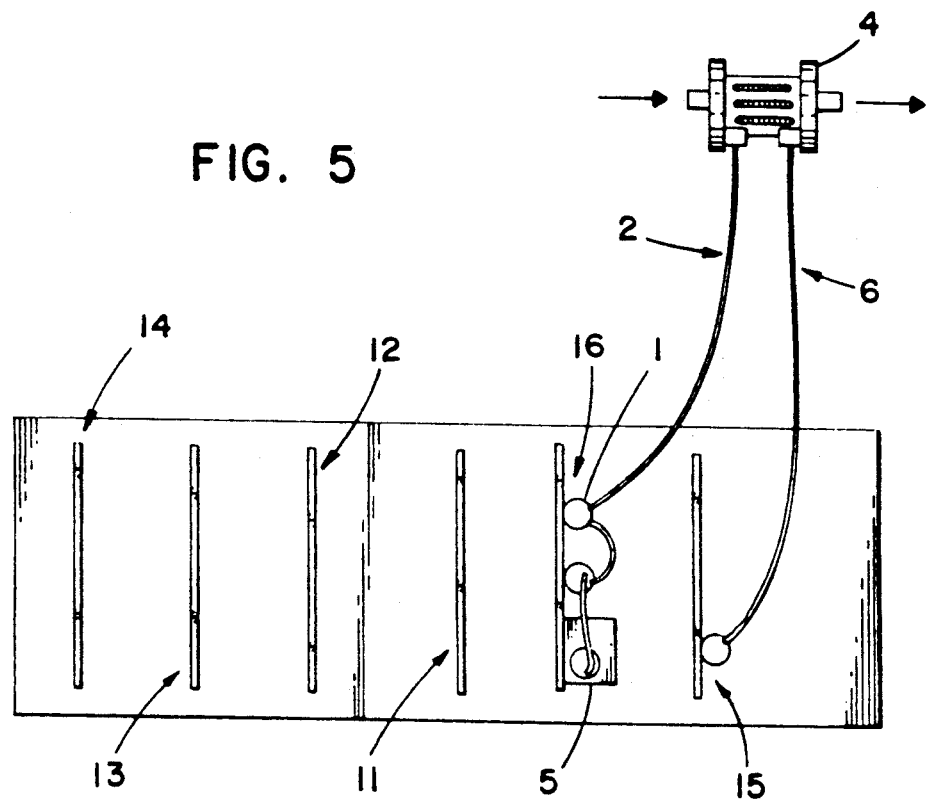
FIG. 5 shows a laser circuit board for the laser with the reference cell.

FIG. 5 shows an alternative instrumental design where a compact measurement cell 4 is connected to the diode laser spectrometer with optical fibers 2. The measurement cell 4 is designed to be integrated in e.g. a patient mouth piece to measure the oxygen contents. The gas flow through the measurement cell 4 is indicated with arrows. The measurement cell 4 is then connected to the receiver card with optical fibers or electrical wires 6.

The instrument is intended to operate completely automatic and therefore the adjustment of laser temperature, bias current, locking to the absorption line, and measurement of the absorption is controlled from a computer, standard PC or equivalent, via an interface 13.

Figure 6:
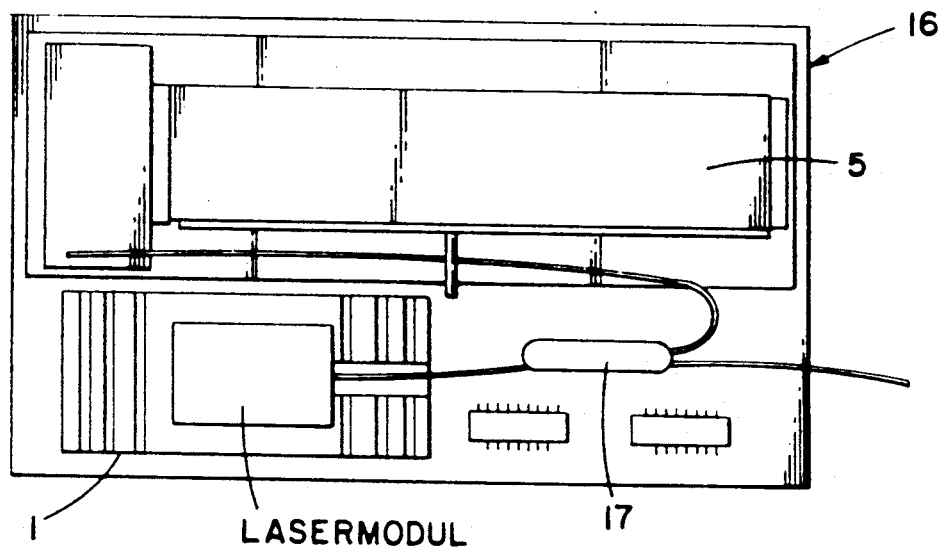
FIG. 6 shows a system with several laser circuits whose output is multiplexed into one fiber for simultaneous measurement of several gases.

On the laser circuit board 16 (FIG. 6) those parts are integrated that determines which gas that is to be measured. A molecule is selected by matching a suitable laser 1 and a reference gas contained in the reference cell 5 integrated on the card. A laser module 1 with fiberpigtail, an optical power divider, reference cell, and electronics is mounted on the laser circuit board 16. The reference cell 5 is used to stabilize the laser to the absorption line and to provide normalization values for the calculation of the gas concentration. By locating the laser and the reference cell on the same card splicing of the fiber to the reference cell is avoided which results in a lower instrumental noise. Moreover, a modular design of the instrument is obtained. The collimated light out from the measurement fiber is centered on wavelength of the absorption line of the gas in the reference cell. This means that measurements can be performed in several different measurement situations, e.g. over an atmospheric path, in an evanescent fiber probe, a specially designed optical probe, or in a conventional measurement cell.

The modular design of the spectrometer means that several laser circuits can be multiplexed on the same fiber, either with wavelength multiplexing or alternatively with time multiplexing there one laser circuit at a time is used. In this way it is possible to measure several gases over the same measurement path. You can also choose to multiplex one laser circuit to several measurement fibers and in this way measure one gas on several different measurement paths that can be located kilometers apart. Several components suitable for this multiplexing have been developed in the area of optical fiber communication.

FIG. 7 shows a device where laser circuits 16a-d, each tuned to an absorption line, are multiplexed into a common measurement fiber 18 by using a fiber multiplexer 17.

Another way of avoiding free air paths in the instrument and obtain a compact design is to use glass prisms for light distribution between laser and reference cell and for splitting the light to a measurement and a reference path.

Figure 8:
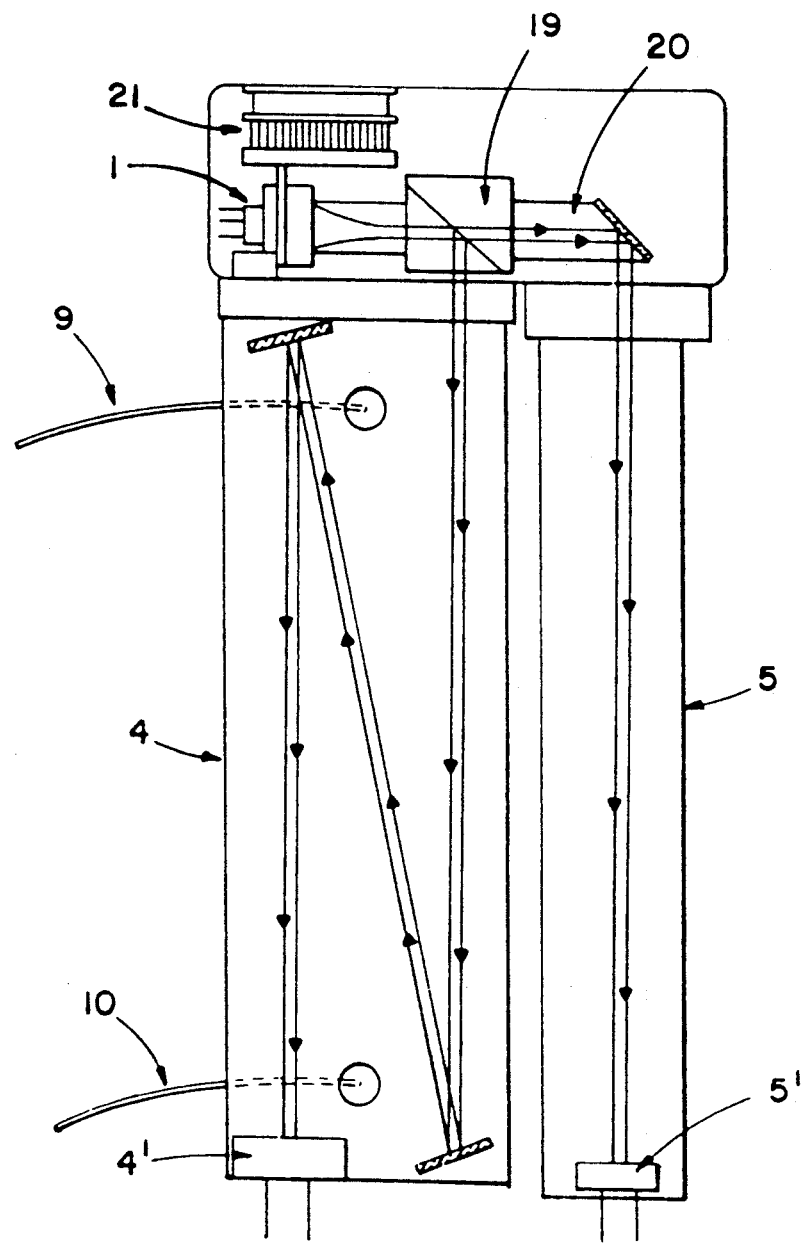
FIG. 8 shows a schematic of the basic apparatus design using glass prisms for light distribution.

Such an arrangement is shown in FIG. 8 where the laser light from the laser 1 is distributed to measurement cell 4 and the reference cell 5 by means of beamsplitter 19 and a glass prism 20, and passed on to the detectors of the measurement 4' and reference 5' cells.

Other parts of the arrangement are in and outgoing flexible tubes, 9 and 10, to the measurement cell 4 and a peltier cooler 21.

Figure 9:
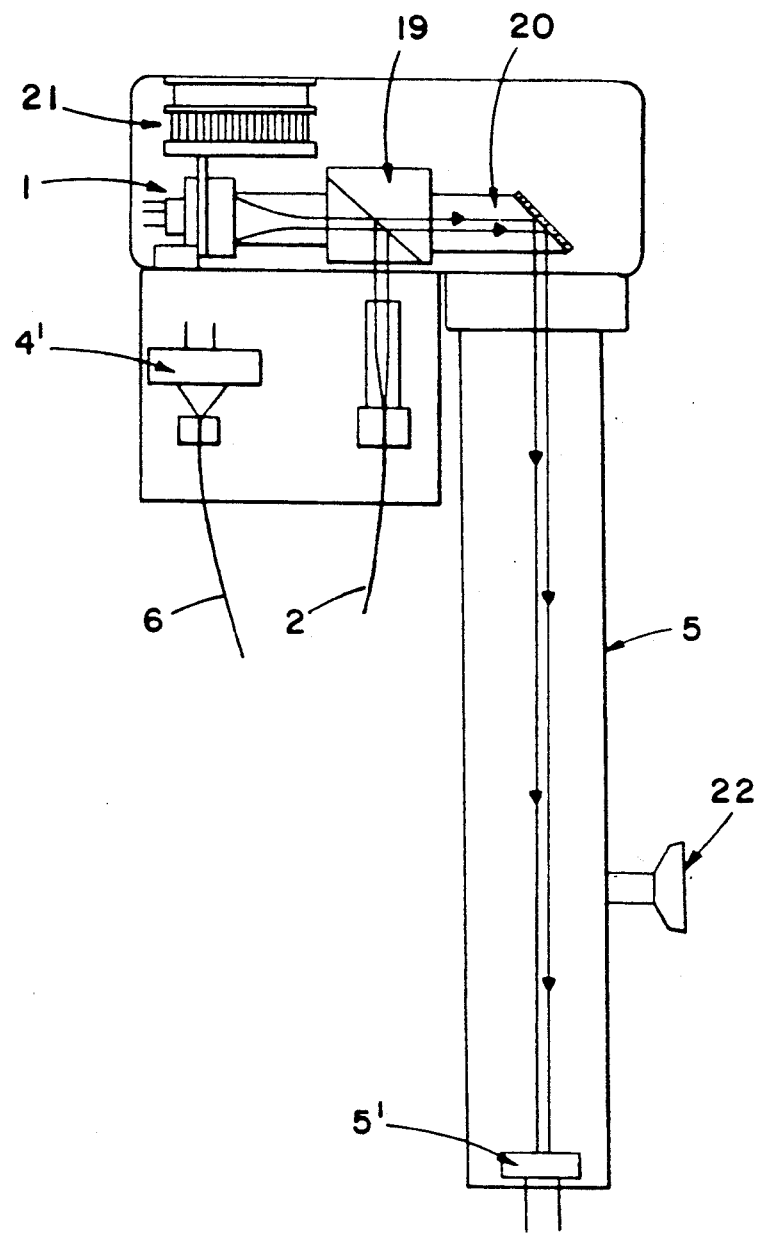
FIG. 9 shows a schematic of the basic apparatus design using both glass prisms and optical fibers.

FIG. 9 shows a modified arrangement according to which the instrument can be connected to a compact optical probe of the type shown in FIG. 4 using optical fibers 2 and 6. A seal-off valve to the reference cell is marked with 22.

A single-mode fiber 2 is connected to the optical probe to maintain good beam quality while a multimode fiber 6 is preferable to pass the light back from the optical probe to collect as much light as possible.

Two different methods can be used for the signal conditioning depending on what degree of instrumental complexity that can be accepted.

In the first method, transmission compensation followed by lock-in detection, which is schematically illustrated in FIG. 10, the laser is modulated with a triangular wave which is obtained directly from the digital unit and the received signal is demodulated in two steps. Before the phase sensitive lock-in detection an analog signal conditioning is performed 32, where the signal from the monitor photodiode of the laser is used to compensate the measurement signal for unwanted attenuation caused by environmental influences in the measurement path and in the optics of the instrument. The harmonics of the received intensity, which is modulated by the absorption line, is thereafter detected with phase sensitive demodulators (lock-in detection). The intensity variations of the resulting normalized signal will then only by dependent of molecular absorption as described in the invented signal conditioning.

The reference signals to the phase sensitive demodulators can be either square-wave or sine-wave, preferably square-wave. The phase difference between the received modulation signals and the reference signals is optimized automatically by a computer. The phase difference between these signals can also be used to determine the length of the measurement path, a value needed for the gas concentration calculation. The information from the signal on the second harmonic $2f_o$ is fed to an analog multiplexer and an A/D-converter for calculation of the gas concentration. Information from the third harmonic $3f_o$ is used to stabilize the laser to the center of the-absorption line via a PID-regulator. This signal is also transferred to the computer to verify that the laser operates at the proper wavelength.

Figure 11A:
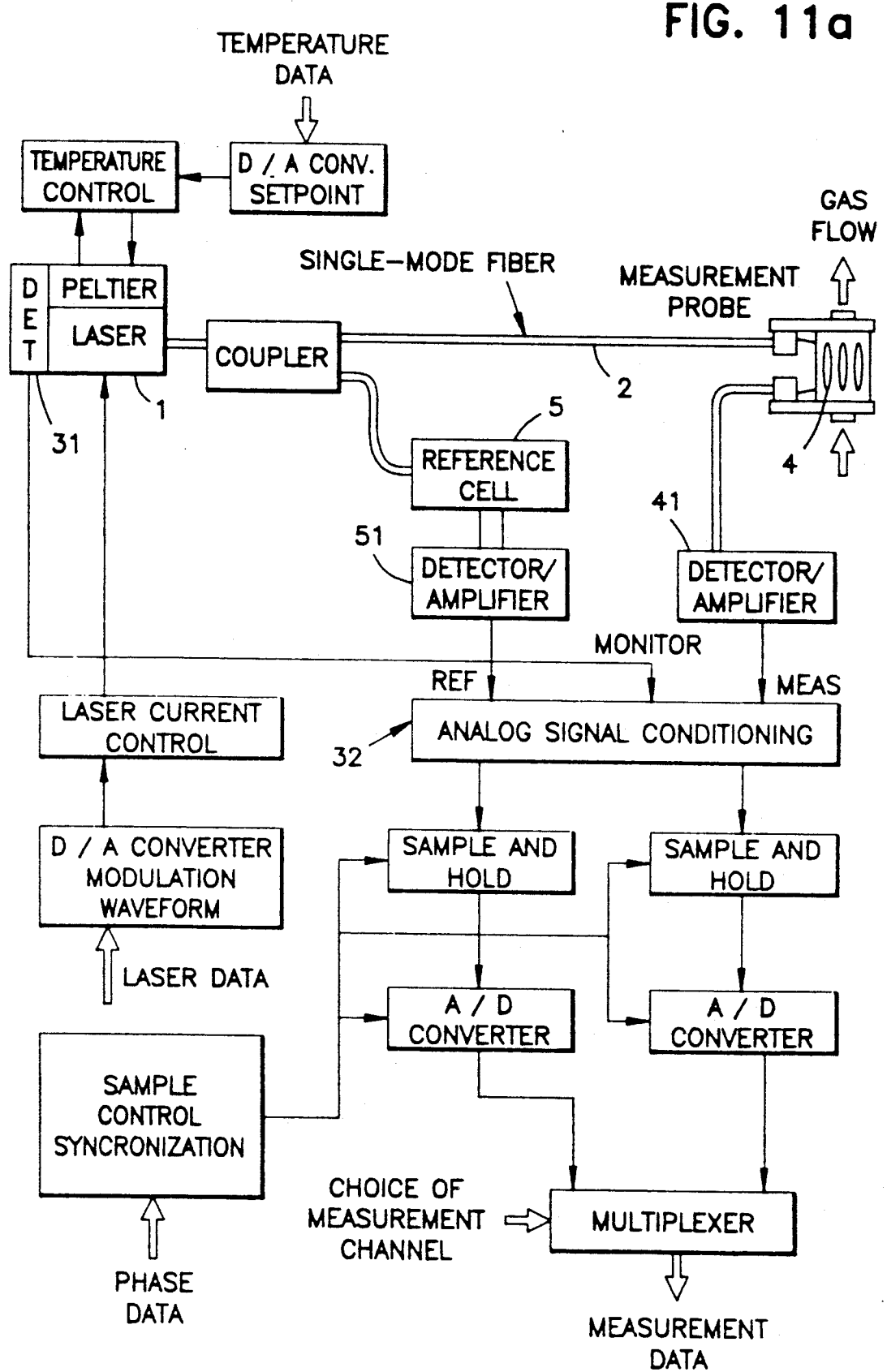
FIG. 11a and FIG. 11b, collectively referred to herein as FIG. 11, show a block diagram of the measurement system using digital modulation and measurement control.
Figure 11B:
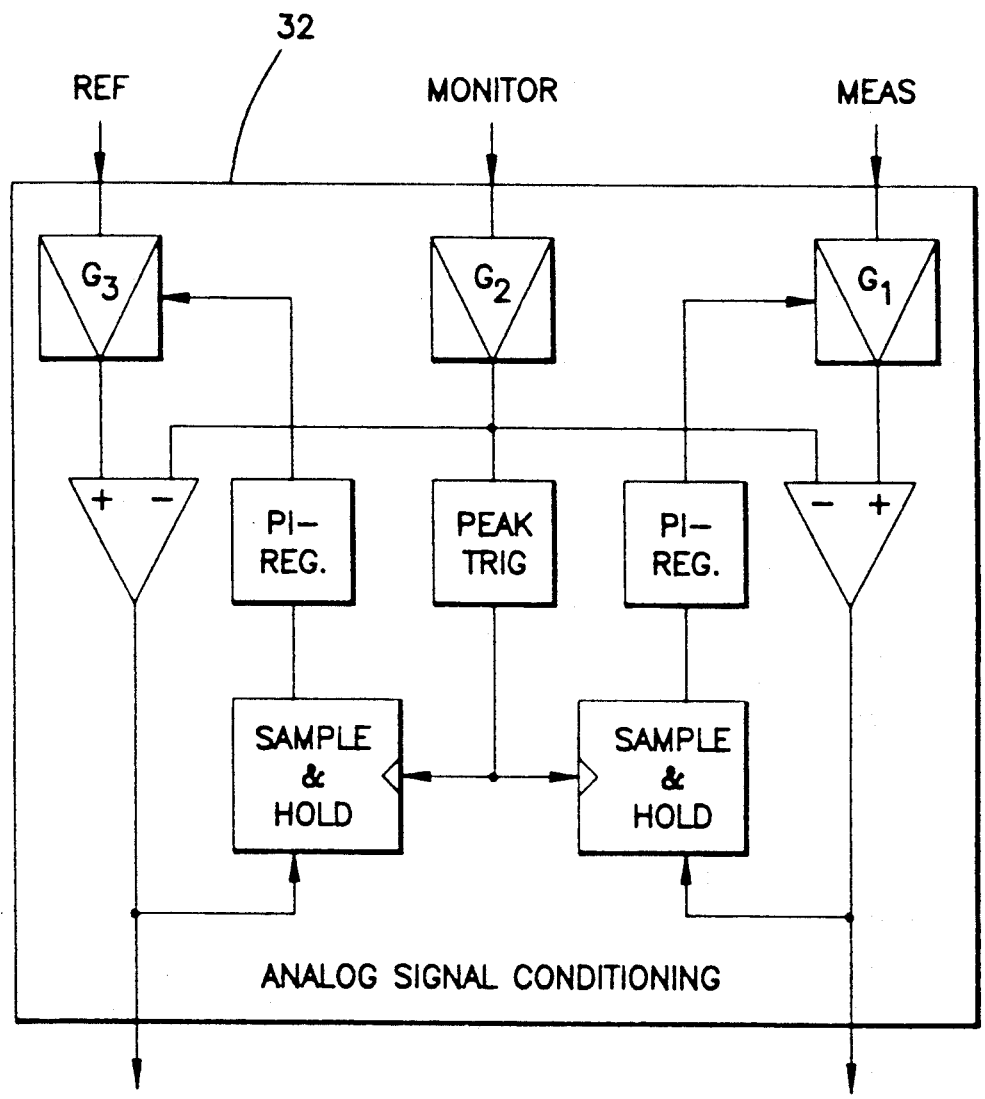

The second measurement method, schematically shown in FIG. 11, uses digital modulation and measurement and is based on that the laser is modulated with a special waveform and that the amplitude of the measurement and reference signals are sampled with an A/D-converter. The gas concentration is then calculated in the computer. Information about the laser wavelength compared to the absorption line is extracted from these sampled values and the laser bias current and temperature is adjusted accordingly. The signal analysis is of the same type as that used in ref 8, but with the important difference that we use a preprocessing with analog signal conditioning to compensate for nongas-related attenuation, which results in higher measurement accuracy. The signal from the measurement cell 4 is fed back to the electronic unit using a multi-mode fiber or alternatively the detector can be located in the measurement cell and the signal led back using ordinary electrical cables. In AlGaAs and InGaAsP lasers a considerable intensity modulation is obtained together with the frequency modulation. In the invention this is used to automatically compensate for nongasrelated variations in the transmission in the measurement path or in the optics of the instrument.

Measurement cell

In certain measurement applications it is important to have a very compact measurement cell. This can be realized by "folding" the cell a large number of times. Each time this folding occurs means that the beam is reflected against a mirror which adds losses into the beam path. These losses must be kept low and moreover, they are not allowed to be strongly dependent of the optical wavelength. The minimum cell acceptable cell transmission is set by the signal-to-noise ratio (SNR) required.

One type of mirror that can be used here is dielectric mirrors. They have a limited wavelength range but apart from that they have very good spectral characteristics including low losses.

Figure 12:
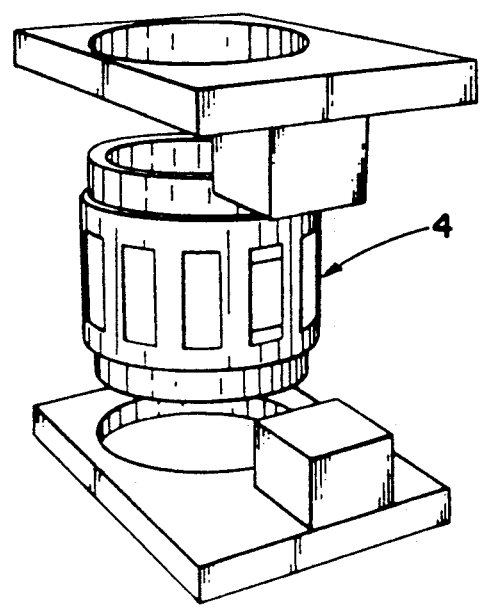
FIG. 12 shows, in perspective, an exploded view of the optical measurement probe.
Figure 13A:
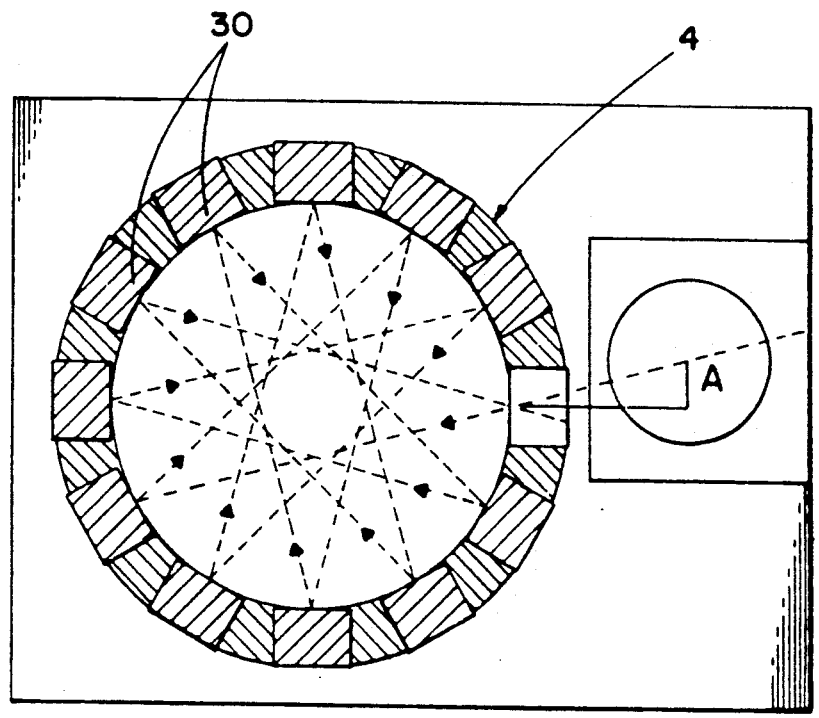
FIG. 13a shows a horizontal sectional view through the measurement probe and FIG. 13b a vertical sectional view through its lower part.
Figure 13B:
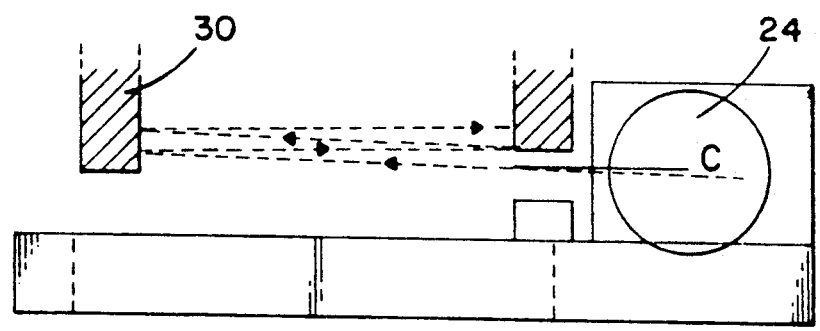

FIG. 12 shows in perspective the measurement optical probe and FIG. 13 shows a sectional view through it to illustrate the beam path.

The measurement optical probe consists of a cylindrical measurement volume, with dimensions e.g. 20×20 mm. The cylinder is divided into 12 segments each of 30 degrees which each contains a dielectric mirror having a reflectance of at least 98%. The beam will be reflected 36 times in the probe which corresponds to a maximum attenuation of $0.98^{36} = 0.48$ (3.2 dB). The probe is fed from a singel-mode fiber (typical 5/125 mm) and a lens which creates a parallel beam with a diameter of approximately 0.8 mm. The effective path length in the probe is approximately 70 cm. The detection of the outcoming beam is either performed directly on a photodiode mounted in the probe or via a fiber with large core diameter in which case the photodiode can be located far away from the measurement volume.

A unit 24 for coupling of the light into the optical probe enables the alignment of the beam with a sufficient number of degrees of freedom.

The material of the measurement optical probe can be aluminum, stainless steel, or a ceramic.

Another type of optical probe is an optical fiber where the evanescent field which propagates outside the core is used. When light propagates in an optical fiber the main part of it is confined to the core but a certain part also propagates in the cladding (the evanescent field). By using a specially designed fiber that only consists of a core and letting this fiber be surrounded by a fluid that constitutes the cladding (or alternatively let a surrounding gas constitute the cladding) the evanescent field and thereby also the total optical field will be influenced in a similar way as when light propagates over an atmospheric path. In this way it is possible to determine the concentration of a specific gas in a surrounding atmosphere or fluid. Furthermore, OTDR (Optical Time Domain Reflectometry) can be used to localize point emissions along an evanescent fiber probe.

Fiber adapter

It must be possible to align the fiber tip so that the light beam after passage through the measurement cell 4 or the reference cell 5 impinges upon the photodetector (or outcoupling fiber). This is obtained using a fiber tip equipped with a spherical adapter. This arrangement provides sufficient number of degrees of freedom in the alignment. The fiber is aligned once and for all and then locked with a clamping screw.

Reference cell

Figure 14:
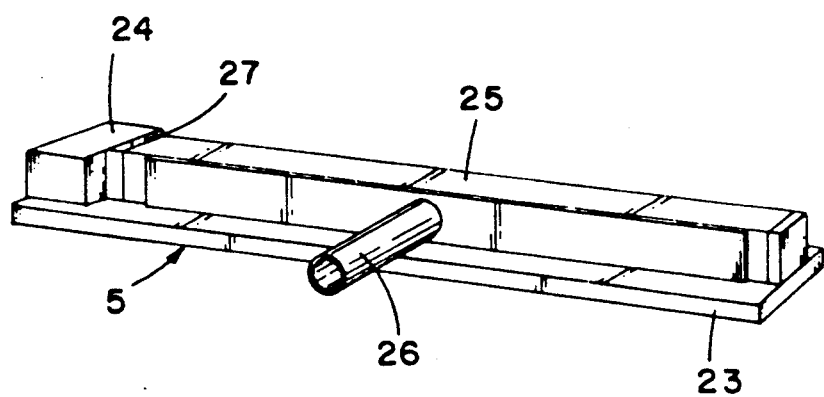
FIG. 14 shows, in perspective, a reference cell.

FIG. 14 shows in perspective the reference cell 5 which consists of a rigid plate 23, an incoupling unit 24 and the measurement volume 25. According to one design it has an effective length of 10 cm and is constructed for 8 passages, i.e. a total measurement path of 80 cm. A seal-off valve 26 and a quartz window 27 between the incoupling unit 24 and the cell is also included in the reference cell.

Figure 15:
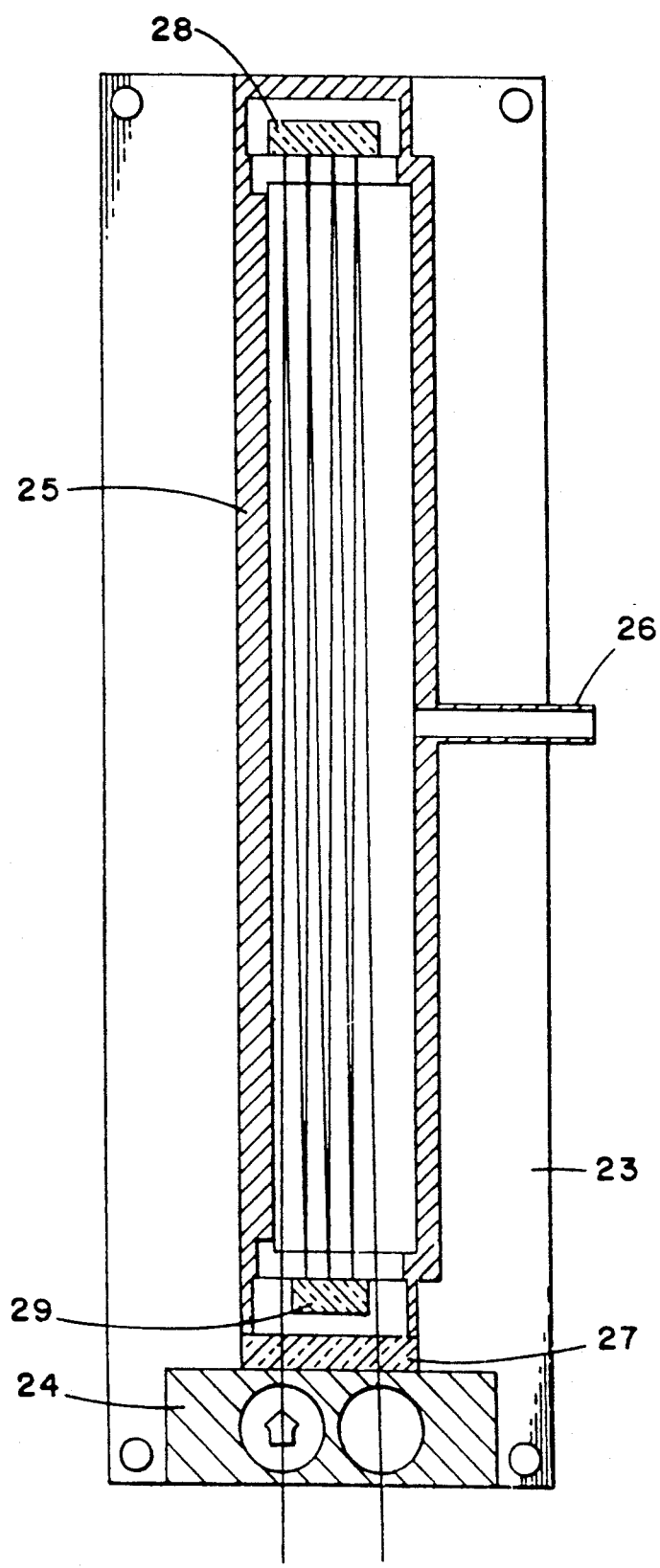
FIG. 15 shows, in a larger scale, a section through the reference cell.

FIG. 15 shows in a larger scale a section through the reference cell. Two dielectric mirrors 28 and 29 with high reflectivity (typically better then 0.98) is mounted at both ends of the cell. In this example the reference beam is reflected 7 times corresponding to a total attenuation of $0.98^7 = 0.87$ (0.6 dB). The base plate 23 is designed to fit onto a standard europe circuit board.

What is claimed is:

1. A spectroscopic method for measuring the concentration of a gas in a gas sample, the method comprising the steps of:
    intensity modulating a light of a laser diode and frequency modulating the light by a modulation signal to lock the modulated light to an absorption line of a gas within a reference cell of a predetermined pressure and concentration;
    passing the modulated light through the gas sample along a measurement path and through the reference cell;
    detecting intensity of the light passed through the gas sample and the reference cell and generating a measurement signal and a reference signal, respectively, representative thereof;
    automatically compensating the measurement signal for nongasrelated transmission variations in the measurement path by a first and second demodulating step, and first demodulating step comprising the steps of:
        forming a first difference signal between a monitoring signal representative of the modulated light and the measurement signal,
        forming a second difference signal between the monitoring signal and said reference signal, and
        automatically adjusting a first and second gain level of the measurement signal and the reference signal such that the first and second difference signals are equal to zero with respect to an amplitude of a fundamental frequency of the modulation signal,
    said second demodulating step comprising the steps of:
        detecting harmonics of the measurement signal and reference signal with respect to the fundamental frequency of the modulation signal;
    receiving the compensated and demodulated measurement signal and reference signal and generating a concentration signal which is indicative of the concentration of the gas in the gas sample.

2. A method according to claim 1, wherein the laser diode is current modulated with a triangular signal in audio frequency range from a digital modulation and control unit.

3. A method according to claim 2, wherein demodulating the measurement and reference signal further comprise the steps of:
    using the intensity modulation of the laser diode and the monitor signal from a monitor photodiode of the laser to automatically compensate for nongasrelated transmission variations without using a baseline of a spectrum; and
    detecting the harmonics by performing lock-in detection with digital reference signals from the digital modulation and control unit; and
    wherein the step of generating a concentration signal further comprises the step of dividing the demodulated measurement signal with the demodulated reference signal.

4. A method according to claim 1, further wherein a phase difference between the measurement signal and reference signal is used to determine the length of the measurement path for use in generating the concentration signal.

5. A method according to claim 1, further wherein the laser diode is modulated with a frequency (f), the measurement signal is demodulated with a double or quadruple frequency (2f or 4f) and a signal generated by demodulating the measurement signal with a triple frequency (3f) provides feedback for locking the laser diode to the absorption line of the gas at the predetermined pressure and concentration.

6. A method according to claim 1, further wherein pressure, temperature and/or magnetic and electric field strength is determined by detecting a relationship of these parameters to parameters of the absorption line.

7. A spectroscopic method to measure the concentration of a gas in a gas sample, the method comprising the steps of:
    intensity modulating a light of a laser diode and frequency modulating the light by performing stepwise modulation with a modulation signal;
    passing the modulated light through the gas sample along a measurement path and through a reference cell of a predetermined pressure and concentration;
    detecting intensity of the light passed through the gas sample and the reference cell and generating a measurement signal and a reference signal, respectively, representative thereof;
    automatically compensating the measurement signal for nongasrelated transmission variations in the measurement path by a first and second demodulating step, said first demodulating step comprising the steps of:
        forming a first difference signal between a monitoring signal representative of the modulated light and the measurement signal,
        forming a second difference signal between the monitoring signal and said reference signal, and
        automatically adjusting a first and second gain level of the measurement signal and the reference signal such that the first and second difference signals are equal to zero with respect to an amplitude of a fundamental frequency of the modulation signal, said second demodulation step comprising the step of:
sampling the measurement signal and reference signal at corresponding points on an absorption spectrum after compensation of the measurement and reference signal, receiving the sampling of the reference and measurement signal and generating a concentration signal which is indicative of the concentration of the gas in the gas sample.

8. An apparatus for spectroscopic measurement of a concentration of a gas in a gas sample, comprising:
means for intensity and frequency modulating a light of a laser diode by a modulation signal to lock the light to an absorption line of a gas within a reference cell of a predetermined pressure and concentration;
means for distributing the modulated light through the gas sample along a measurement path and through the reference cell;
means for detecting the intensity of the light passed through the gas sample and the reference cell and for generating a measurement signal and a reference signal, respectively, representative thereof;
means for automatically compensating the measurement signal for nongasrelated transmission variations in the measurement path, the compensation means comprising:
means for forming a first difference signal between a monitoring signal from a monitor diode representative of the modulated light from said laser and the measurement signal,
means for forming a second difference signal between the monitoring signal and said reference signal, and
means for automatically adjusting a first gain level of the measurement signal and a second gain level of the reference signal such that the first and second difference signals are equal to zero with respect to an amplitude of a fundamental frequency of the modulation signal;
means for detecting the harmonics of the measurement signal and reference signal with respect to the fundamental frequency of the modulation signal; and
means for receiving the harmonics of the compensated measurement signal and reference signal and for generating a signal which is indicative of the concentration in the gas sample.

9. An apparatus according to claim 8, wherein said distribution means comprises optical fibers and/or glass prisms to avoid unwanted interference from atmosphere;
wherein said modulating means modulates the laser with a periodic triangular audio frequency signal; and
wherein said compensation means comprises a signal conditioning unit provided with inputs for said monitoring signal from said monitor diode, for said measurement signal from said detection means, and for said reference signal from said detection means, the signal conditioning unit further comprising a first and second controllable amplifier for receiving the measurement signal and reference signal, respectively, and outputs of the first and second controllable amplifier connected to a first and second differential amplifier, respectively, the different amplifiers having outputs connected to a first and second sample and hold circuits, respectively, which are each triggered from a peak detector which detects peak values of said monitor signal, output signals from said first and second sample and hold circuit are filtered by a first and second filter circuit, respectively, to generate a first and second control signal for setting said first and second gain of the controllable amplifiers, respectively.

10. An apparatus according to claim 8, wherein the measurement is performed in a measurement cell to which the modulated light is distributed, the measurement cell having reflecting means to reflect the laser beam a plurality of times increasing an effective length of the measurement path inside the measurement cell.

11. An apparatus according to claim 10, wherein the measurement cell is formed as a cylindrical tube and said reflecting means comprises a plurality of segments, each segment containing reflective elements arranged to reflect the light in a plurality of planes inside the measurement cell such that the beam pattern automatically repeats itself in consecutive planes.

12. An apparatus according to claim 8, wherein the reference cell comprises reflective elements to reflect the light a plurality of times inside the reference cell.

13. An apparatus according to claim 8, wherein the measurement is performed in a measurement cell to which the modulated light is distributed, coupling means is provided at the measurement cell to align the light such that the light has a certain degree of angular freedom.

14. An apparatus according to claim 13, wherein the measurement cell is formed as a cylindrical tube and said reflecting means comprises a plurality of segments, each segment containing reflective elements arranged to reflect the light in a plurality of planes inside the measurement cell such that a beam pattern automatically repeats itself in consecutive planes.

* * * * *

UNITED STATES PATENT AND TRADEMARK OFFICE
CERTIFICATE OF CORRECTION

PATENT NO. : 5,173,749

DATED : 22 December 1992

INVENTOR(S) : Tell et al.

It is certified that error appears in the above-identified patent and that said Letters Patent is hereby corrected as shown below:

On the title page, item [73]: Assignee, delete "Gothenburg" and insert --Göteborg--.

In column 1, line 32, delete "of" and insert --to--.

In column 1, line 40, delete "of" after the word "cooling".

In column 2, lines 55 and 56, delete "Offenlengungsschrift" and insert --Offenlegungsschrift--.

In column 3, line 11, delete "different" and insert --difference--.

In column 4, line 15, delete "the" after the word "and".

In column 7, line 38, insert --two-- after the word "into".

In column 10, line 50, insert --*-- after the symbol "*".

UNITED STATES PATENT AND TRADEMARK OFFICE
CERTIFICATE OF CORRECTION

PATENT NO. : 5,173,749
DATED : 22 December 1992
INVENTOR(S) : Tell et al.

It is certified that error appears in the above-identified patent and that said Letters Patent is hereby corrected as shown below:

In column 10, line 58, insert a dash -- - -- before the "H" at the beginning of the line.

In column 10, line 62, delete "$V=V_oH_1\rightarrow$" and insert --$V=V_o\rightarrow H_1$--.

In column 12, line 12, delete " ' " after the word "diode".

Signed and Sealed this

Twenty-ninth Day of March, 1994

Attest:

*Attesting Officer*

BRUCE LEHMAN

*Commissioner of Patents and Trademarks*